United States Patent [19]
Baxter et al.

[11] Patent Number: 5,955,435
[45] Date of Patent: Sep. 21, 1999

[54] PEPTIDYL COMPOUNDS HAVING MMP AND TNF INHIBITORY ACTIVITY

[75] Inventors: Andrew Douglas Baxter; John Gary Montana, both of Cambridge, United Kingdom

[73] Assignee: Darwin Discovery Limited, United Kingdom

[21] Appl. No.: 08/908,990

[22] Filed: Aug. 8, 1997

[30] Foreign Application Priority Data

Aug. 8, 1996 [GB] United Kingdom ................... 9616643

[51] Int. Cl.⁶ .................................................... A61K 38/05
[52] U.S. Cl. .............................. 514/19; 514/18; 530/331; 562/445
[58] Field of Search ........................ 514/19, 18; 530/331; 562/445

[56] References Cited

FOREIGN PATENT DOCUMENTS

| 9509833 | 4/1995 | WIPO . |
| 9513289 | 5/1995 | WIPO . |
| 9519961 | 7/1995 | WIPO . |
| 9611209 | 4/1996 | WIPO . |

OTHER PUBLICATIONS

Holmquist, B., B.L. Vallee (1980) Metal–coordinating substrate analogs as inhibitors of metalloenzymes. Chemical Abstracts 92: abstract No. 89874h.

Mori, T. et al. (1979) Comparative studies on protective effect of various sulfhydryl compounds against cell death and DNA strand breaks induced by x–rays in cultured mouse L cells. Chemical Abstracts 91: abstract No. 32686y.

Isomura, Y. et al. (1992) Preparation of amide derivatives as collagenase inhibitors. Chemical Abstracts 117: abstract No. 212156q.

Corey, E.J., S. Hashimoto (1981) A practical process for large–scale synthesis of (S)–5–hydroxy–6–trans–8,11, 14–cis–eicosatetraenoic acid (5–HETE). Chemical Abstracts 95: abstract No. 24207k.

*Primary Examiner*—Cecilia J. Tsang
*Assistant Examiner*—David Lukton
*Attorney, Agent, or Firm*—Saliwanchik, Lloyd & Saliwanchik

[57] ABSTRACT

Peptidyl compounds have therapeutic utility via MMP and TNF inhibitory activity.

17 Claims, No Drawings

PEPTIDYL COMPOUNDS HAVING MMP AND TNF INHIBITORY ACTIVITY

FIELD OF THE INVENTION

This invention relates to a novel class of peptidyl derivatives, to processes for their preparation, and to their use in medicine.

BACKGROUND OF THE INVENTION

Metalloproteinases, including matrix metalloproteinase (MMP), (human fibroblast) collagenase, gelatinase and TNF convertase (TACE), and their modes of action, and also inhibitors thereof and their clinical effects, are described in WO-A-9611209, WO-A-9712902 and WO-A-9719075, the contents of which are incorporated herein by reference. MMP inhibitors may also be useful in the inhibition of other mammalian metalloproteinases such as the adamalysin family (or ADAMs) whose members include TNF convertase (TACE) and ADAM-10, which can cause the release of TNFA from cells, and others, which have been demonstrated to be expressed by human articular cartilage cells and also involved in the destruction of myelin basic protein, a phenomenon associated with multiple sclerosis.

Compounds which have the property of inhibiting the action of metalloproteinases involved in connective tissue breakdown, such as collagenase, stromelysin and gelatinase, have been shown to inhibit the release of TNF both in vitro and in vivo. See Gearing et al(1994), Nature 370:555–557; McGeehan et al (1994), Nature 370:558–561; GB-A-2268934; and WO-A-9320047. All of these reported inhibitors contain a hydroxamic acid zinc-binding group, as do the imidazole-substituted compounds disclosed in WO-A-9523790. Other compounds that inhibit MMP and/or TNF are described in WO-A-9513289, WO-A-9611209, WO-A-96035687, WO-A-9603571 1, WO-A-96035712 and WO-A-96035714.

MMP inhibitors are also disclosed in WO-A-9509833 and WO-A-9519961.

SUMMARY OF THE INVENTION

The invention encompasses novel compounds of formula (I) which are useful inhibitors of matrix metalloproteinases and/or TNFα mediated diseases including degenerative diseases (such as defined above) and certain cancers.

According to the invention, novel compounds are of general formula (I):

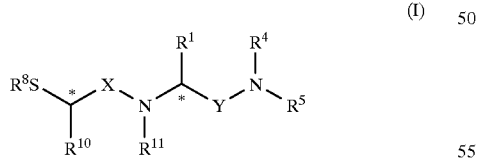

(I)

wherein:

X and Y may be C=O or C=S and may be the same or different; Y may also be $S(O)_m$ where m=1–2;

$R^1$ is $C_{0-4}$-alkyl-$R^2$;

$R^2$ is aryl substituted with $R^3$ or heteroaryl optionally substituted with $R^3$ (heteroaryl does not include unsubstituted 3-indolyl);

$R^3$ may be $C_{1-4}$-alkyl, aryl, heteroaryl, halogen, $OR^6$ (except when $R^2$ is aryl), $N(R^6)_2$ where $R^6$ may be the same or different, $CO_2R^7$, $COR^6$, $CON(R^6)_2$ (where $R^6$ may be the same or different), $SO_nR^6$ (where n is 0–2 and $R^6$ is not H), $SO_2N(R^6)_2$ (where $R^6$ may be the same or different), $NR^6COR^6$ (where $R^6$ may be the same or different), $NR^6CO_2R^7$ (where $R^7$ is not H), $NR^6CON(R^6)_2$ (where $R^6$ may be the same or different) or $NR^6SO_2R^6$ (where $R^6$ may be the same or different). $R^3$ may also be a $C_{1-4}$-alkyl group substituted by any group previously defined in $R^3$;

$R^4$ and $R^5$ may be the same or different taken from H or $C_{1-4}$ alkyl;

$R^6$ is H, $C_{1-4}$-alkyl, aryl, $C_{1-4}$-alkyl-aryl, heteroaryl or $C_{1-4}$-alkyl-heteroaryl;

$R^7$ is H, $C_{1-4}$-alkyl, $C_{1-4}$-alkyl-aryl, or $C_{1-4}$-alkyl-heteroaryl;

$R^8$ is H or the group $COR^9$;

$R^9$ is $C_{1-4}$ alkyl, aryl, heteroaryl, $C_{1-4}$ alkyl-aryl or $C_{1-4}$ alkyl-heteroaryl;

$R^{10}$ and $R^{11}$ may be the same or different taken from the groups, H, $C_{1-6}$ alkyl, (optionally substituted with $R^{12}$), aryl (optionally substituted with $R^{12}$), $C_{1-6}$ alkyl-aryl (optionally substituted with $R^{12}$), heteroaryl (optionally substituted with $R^{12}$), $C_{1-6}$ alkyl-heteroaryl (optionally substituted with $R^{12}$), cyclo($C_{3-6}$)alkyl (optionally substituted with $R^{12}$), $C_{1-6}$ alkyl-cyclo($C_{3-6}$)alkyl (optionally substituted with $R^{12}$), heterocyclo($C_{4-6}$)alkyl (optionally substituted with $R^{12}$) or $C_{1-4}$ alkyl-heterocyclo($C_{4-6}$)alkyl (optionally substituted with $R^{12}$);

$R^{12}$ is $COR^{13}$, $NR^6R^{14}$, the group $AR^9$ where A is O, $NR^9$ or $S(O)_n$ where n=0–2, if $A=NR^9$ the groups $R^9$ may be the same or different, phthalimido or the groups:

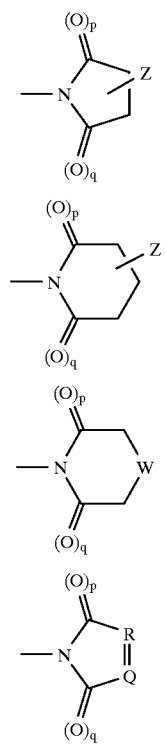

-continued

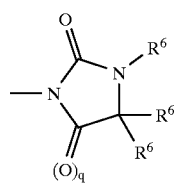

p and q may be 0 or 1 and may be the same or different;

R and Q may be CH or N and may be the same or different;

W may be O, $S(O)_n$ where $n=0-2$ or $NR^{15}$;

Z may be H or $C_{0-4}$ alkyl-$R^{18}$ and may be attached to any available position on the ring;

$R^{13}$ is $OR^7$, $N(R^6)_2$ where $R^6$ may be the same or different, $C_{1-4}$ alkly, aryl, $C_{1-4}$ alkyl-aryl, heteroaryl or $C_{1-4}$ alkyl-heteroaryl;

$R^{14}$ may be $COR^6$, $CO_2R^7$ (where $R^7$ is not H), $CON(R^6)_2$ where $R^6$ may be the same or different, $SO_2R^{16}$, or $COR^{16}$;

$R^{15}$ is H, $C_{1-4}$ alkyl, $COR^9$, $CO_2R^{19}$, $CON(R^6)_2$ where $R^6$ may be the same or different or $SO_2R^9$;

$R^{16}$ is $C_{1-4}$ alkyl (optionally substituted with $R^{17}$);

$R^{17}$ may be $CO_2R^6$, $CON(R^6)_2$ where $R^6$ may be the same or different, $N(R^6)_2$ where $R^6$ may be the same or different, $SO_2R^9$ or the groups:

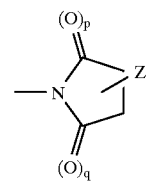

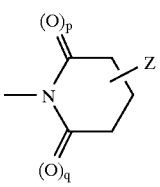

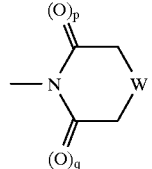

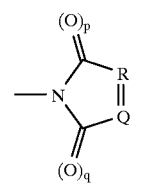

-continued

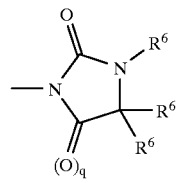

$R^{18}$ is $CO_2R^6$, $CON(R^6)_2$ where $R^6$ may be the same or different, $N(R^6)_2$ where $R^6$ may be the same or different, $NHCO_2R^{19}$, $NHSO_2R^9$ or $NHCOR^9$;

$R^{19}$ is $C_{1-4}$ alkyl, $C_{1-4}$ alkyl-aryl or $C_{1-4}$ alkyl-heteroaryl;

and the salts, solvates, hydrates and protected amino or protected carboxy derivatives thereof.

Combinations of substituents and/or variables are only permissible if such combinations result in stable compounds.

DESCRIPTION OF THE INVENTION

Preferred compounds of the invention comprises those in which one or more of the following apply:

X is C=O;

Y is C=O or $SO_2$;

$R^{10}$ and $R^{11}$ are the same or different and are selected from H and optionally-substituted alkyl, alkyl-aryl, alkyl-heteroaryl, alkyl-cycloalkyl or alkyl-heterocycloalkyl; and $R^{12}$ is $NR^6R^{14}$, phthalimido or any of the said groups.

It will be appreciated that the compounds according to the invention can contain one or more asymmetrically substituted carbon atoms, for example those marked with an asterisk in formula (I). The presence of one or more of these asymmetric centres in a compound of formula (I) can give rise to stereoisomers, and in each case the invention is to be understood to extend to all such stereoisomers, including enantiomers and diastereomers, and mixtures including racemic mixtures thereof.

In the formulae herein, the ~ line is used at a potential asymmetric centre to represent the possibility of R- and S-configurations, the <line and the . . . line to represent a unique configuration at an asymmetric centre.

As used in this specification, alone or in combination, the term "$C_{1-6}$ alkyl" refers to a straight or branched chain alkyl moiety having from one to six carbon atoms, including for example, methyl, ethyl, propyl, isopropyl, butyl, tert-butyl, pentyl, hexyl and the like.

The term "$C_{1-4}$ alkyl" refers to a straight or branched chain alkyl moiety having from one to four carbon atoms, including for example, methyl, ethyl, propyl, isopropyl, butyl, tert-butyl and the like.

The term "$C_{0-4}$ alkyl" refers to a straight or branched chain alkyl moiety having from one to four carbon atoms, including for example, methyl, ethyl, propyl, isopropyl, butyl, tert-butyl and the like. This term also refers to a case where a substituent, $R^2$ is directly bonded such as in $C_{0-4}$-alkyl-$R^2$ and the like;

The term "cyclo ($C_{3-6}$) alkyl" refers to a saturated alicyclic moiety having from three to six carbon atoms and includes for example cyclopropyl, cyclobutyl, cyclopentyl, cyclohexyl and the like.

The term "heterocyclo ($C_{4-6}$) alkyl" refers to a saturated heterocyclic moiety having from three to six carbon atoms and one or more heteroatom from the group N, O, S and includes for example azetidinyl, pyrrolidinyl, tetrahydrofuranyl, piperidinyl and the like.

There term "aryl" means an optionally substituted phenyl or naphthyl group with the substituent(s) being selected, for example, from halogen, trifluoromethyl, $C_{1-6}$ alkyl alkoxy, phenyl and the like.

The term "heteroaryl" refers to aromatic ring systems of five to ten atoms or which at least one atom is selected from the group, O, N, or S and includes for example furanyl, thiophenyl, pyridyl, indolyl, quinolyl and the like.

The term "halogen" means fluorine, chlorine, bromine or iodine.

The terms "protected amino" and "protected carboxy" mean amino and carboxy groups which are protected in a manner familiar to those skilled in the art. For example, an amino group can be protected by a benzyloxycarbonyl, tert-butoxycarbonyl, acetyl or like groups, or in the form of a phthalimido or like group. A carboxyl group can be protected in the form of a readily cleavable ester such as the methyl, ethyl, benzyl or tert-butyl ester.

Salts of compounds of formula (I) include pharmaceutically acceptable salts, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates.

Salts may also be formed with bases. Such salts include salts derived from inorganic or organic bases, for example alkali metal salts such as magnesium or calcium salts, and organic amine salts such as morpholine, piperidine, dimethylamine or diethylamine salts.

When the "protected carboxy" group in compounds of the invention is an esterified carboxyl group, it may be a metabolically labile ester of formula $CO_2R^{20}$ where $R^{20}$ may be an ethyl, benzyl, phenethyl, phenylpropyl, α- or β-naphthyl, 2,4-dimethylphenyl, 4-tert-butylphenyl, 2,2,2-trifluoroethyl, 1-(benzyloxy)benzyl, 1-(benzyloxy)ethyl, 2-methyl-1-propionyloxypropyl, 2,4,6-trimethylbenzyloxymethyl or pivaloyloxymethyl group.

Compounds of the general formula (I) may be prepared by any suitable method known in the art and/or by the following processes, which itself forms part of the invention.

The present invention also provides a process for preparing a compound of general formula (I) as defined above. It will be appreciated that where a particular stereoisomer of formula (I) is required, the synthetic processes described herein may be used with the appropriate homochiral starting material and/or isomers may be resolved from mixtures using conventional separation techniques (eg. HPLC).

The compounds according to the invention may be prepared by the following process. In the description and formulae below the groups $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, R, Q, W, X, Y and Z are as defined above, except where otherwise indicated. It will be appreciated that functional groups, such as amino, hydroxyl or carboxyl groups, present in the various compounds described below, and which it is desired to retain, may need to be in protected form before any reaction is initiated. In such instances, removal of the protecting group may be the final step in a particular reaction. Suitable protecting groups for such functionality will be apparent to those skilled in the art. For specific details see "Protective Groups in Organic Synthesis", Wiley Interscience, T W Greene, P G M Wuts.

The process required for preparing compounds of general formula (I) comprises deprotecting (for example by hydrolysis) a compound of general formula (II)

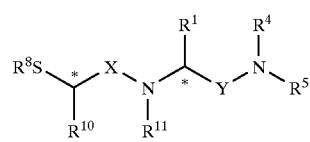

(II)

wherein $R^8$ represents a suitable protecting group (eg tert-butyl, trityl, benzoyl or acetate).

It will be appreciated that where a particular stereoisomer of formula (I) is required, this may be obtained by conventional resolution techniques such as high performance liquid chromatography. Where desired, however, appropriate homochiral starting materials may be used in the coupling reaction to yield a particular stereoisomer of formula (I). This is exemplified below.

When X and Y are C=O, intermediates of general formula (II) may be prepared by coupling an acid of formula (III)

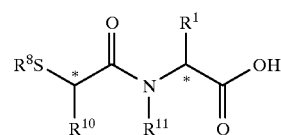

(III)

wherein $R^1$, $R^8$, $R^{10}$ and $R^{11}$ are as defined above, or an active derivative thereof, with an amine of the formula $HNR^4R^5$ (IV) wherein $R^4$ and $R^5$ are defined previously.

Amines of formula (IV) may be commercially available or can be readily obtained from commercially available starting materials using methods known to those skilled in the art. Active derivatives of acids of formula (III) include for example acid anhydrides or acid halides, such as acid chlorides.

The coupling reaction may be performed using standard conditions for amination reactions of this type. Thus, the reaction may be achieved in a solvent, for example an inert organic solvent such as an ether, eg. a cyclic ether such as tetrahydrofuran, an amide eg. a substituted amide such as dimethylformamide, or a halogenated hydrocarbon such as dichloromethane at a low temperature eg. −30° C. to ambient temperature, such as −20° C. to 0° C., optionally in the presence of as base, eg. an organic base such as an amine, eg. triethylamine or a cyclic amine such as N-methylmorpholine. Where an acid of formula (III) is used, the reaction may additionally be performed in the presence of a condensing agent, for example a diimide such as N,N'-dicyclohexylcarbodiimide, advantageously in the presence of a triazole such as 1-hydroxybenzotriazole. Alternatively, the acid may be reacted with a chloroformate for example ethylchloroformate, prior to reaction with the amine of formula (IV).

Similarly, compounds of general formula (II) may be prepared by the coupling of an acid of formula (V)

(V)

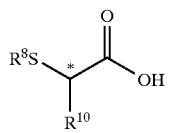

or activated derivative thereof, with an amine of formula (VI)

(VI)

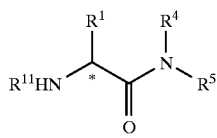

The amine of formula (VI) may be prepared by the coupling of a suitably protected amino-acid of formula (VII)

(VII)

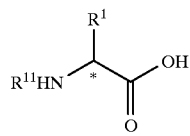

with an amine of formula (IV), followed by the removal of any protecting groups. Suitable protecting groups include carbamates such as benzyloxycarbonyl (Cbz) or tert-butyloxycarbonyl (Boc).

Active derivatives of acids (V) include for example acid anhydrides or acid halides such as acid chlorides as outlined earlier.

The acid of general formula (III) may be prepared by coupling an acid of formula (V), or an active derivative thereof, with an suitably protected amine of formula (VII) followed by removal of any protecting groups as described previously.

α-Thioacetic acids and amino acids and their derivatives such as depicted by general formulae (V) and (VII) respectively can be obtained in optically pure or racemic form. In the homochiral form they provide asymmetric building blocks for the enantiospecific synthesis of compounds of general formula (I). Many of these derivatives can be readily obtained from commercially available starting materials using methods known to those skilled in the art. See "The Practice of Peptide Synthesis" by M. Bodanszk et al, Springer Verlag, New York, (1984) and WO-A-9221360.

Compounds of general formula (II) or (V) may be prepared by nucleophilic substitution of compounds of general formula (VIII) or (IX)

(VIII)

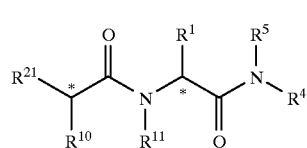

(IX)

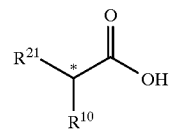

respectively, wherein $R^{21}$ represents a suitable leaving group (eg. a halogen such as bromide, or an alkylsulphonate ester such as methanesulphonate) with a thiol of general formula (X)

$R^8SH$                        (X)

wherein $R^8$ represents a suitable protecting group (eg. tert butyl, trityl, benzoyl or acetate), using standard conditions known to those skilled in the art, as exemplified in WO-A-9005719.

Thiols of general formula (X) may be obtained from commercially available starting materials using methods known to those skilled in the art. Many thiols of general formula (X) are also commercially available.

Compounds of general formula (VIII) may be prepared by coupling an acid of general formula (XI)

(XI)

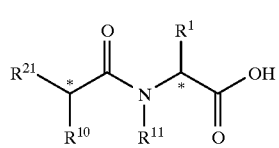

wherein $R^1$, $R^{21}$, $R^{10}$ and $R^{11}$ are as defined above (or suitably protected versions thereof) or an active derivative thereof, with an amine of formula (IV) using similar coupling conditions to those described for the preparation of compounds of formula (II).

Carboxylic acids of the structure depicted in formulae (IX) and (XI) can be obtained in chiral or racemic form. Many of these derivatives can be readily obtained from commercially available starting materials using methods known to those skilled in the art WO-A-9005719.

Where $R^{11}$ is not H and amino acids of general formula (VII) are required, these may be prepared by the nucleophilic displacement of an alkylating agent of formula (XIII) with an amine of formula (XIV)

(XIII)

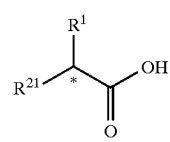

(XIV)

wherein $R^{11}$ and $R^{21}$ have been defined previously.

Intermediates of formula (XIII) may be prepared from amino acids of general formula (VII) by diazotisation under appropriate conditions.

Amines of formula (XIV) may be commercially available or can be readily obtained from commercially available starting materials using methods known to those skilled in the art.

Compounds of formula (I) may also be prepared by interconversion of other compounds of formula (I). Thus, for example, a compound of formula (I) wherein $R^1$ is a $C_{1-4}$ alkyl-$R^2$ may be prepared by hydrogenation (using palladium on carbon in suitable solvent, such as an alcohol, e.g. ethanol) of a compound of formula (I) wherein $R^1$ is a $C_{2-4}$ alkenyl group. As a further example, a compound of formula (I) wherein $R^8$ is a group $R^9$ CO may be prepared by acylation (using a suitable acid chloride $R^9$ COCl, in the presence of a base such as a triethylamine in a suitable solvent, such as a chlorinated solvent, e.g. dichloromethane) of a compound of formula (I) wherein $R^8$ is H.

Compounds where X and Y are C=S may be prepared by thioamidation, for instance with Lawesson's Reagent, of compounds where X and Y are C=O.

Any mixtures of final products or intermediates obtained can be separated on the basis of the pysico-chemical differences of the constituents, in known manner, into the pure final products or intermediates, for example by chromatography, distillation, fractional crystallization, or by formation of a salt if appropriate or possible under the circumstances.

The compounds according to the invention exhibit in vitro inhibiting activities with respect to stromelysin, collagenase and gelatinase. Compounds according to the invention also exhibit in vitro inhibition of TNF release. The activity and selectivity of the compounds may be determined by use of the appropriate enzyme inhibition test, for example as described in Examples A–M hereinafter.

This invention also relates to a method of treatment for patients (including man and/or mammalian animals raised in the dairy, meat or fur industries or as pets) suffering from disorders or diseases which can be attributed to stromelysin as previously described, and more specifically, a method of treatment involving the administration of the matrix metalloproteinase inhibitors of formula (I) as the active constituents.

Accordingly, the compounds of formula (I) can be used among other things in the treatment of osteoarthritis and rheumatoid arthritis, and in diseases and indications resulting from the over-expression of these matrix metalloproteinases such as found in certain metastatic tumour cell lines.

As mentioned above, compounds of formula (I) are useful in human or veterinary medicine since they are active as inhibitors of TNF and MMPs. Accordingly in another aspect, this invention concerns:

a method of management (by which is meant treatment of prophylaxis) of disease or conditions mediated by TNF and/or MMPs in mammals, in particular in humans, which method comprises administering to the mammal an effective, amount of a compound of formula (I) above, or a pharmaceutically acceptable salt thereof; and a compound of formula (I) for use in human or veterinary medicine, particularly in the management (by which is meant treatment or prophylaxis) of diseases or conditions mediated by TNF and/or MMPs; and the use of a compound of formula (I) in the preparation of an agent for the management (by which is meant treatment or prophylaxis) of diseases or conditions mediated by TNF and/or MMPs.

The disease or conditions referred to above include inflammatory diseases, autoimmune diseases cancer, cardiovascular diseases, diseases involving tissue breakdown such as rheumatoid arthritis, osteoarthritis, osteoporosis, neurodegeneration, Alzheimer's disease, atherosclerosis, congestive heart failure, stroke, vasculitis, Crohn's disease, ulcerative colitis, multiple sclerosis, periodontitis, gingivitis and those involving tissue breakdown such as bone resportion, haemorrhage, coagulation, acute phase response, cachexia and anorexia, acute infections, HIV infections, fever, shock states, graft versus host reactions, dermatological conditions, surgical wound healing, psoriasis, atopic dermatitis, epidermolysis bullosa, tumour growth, angiogenesis and invasion by secondary metastases, ophthalmological disease, retinopathy, corneal ulceration, reperfusion injury, migraine, meningitis, asthma, rhinitis, allergic conjunctivitis, eczema, anaphylaxis, restenosis, endometriosis, and endosclerosis.

For the treatment of rheumatoid arthritis, osteoarthritis, and in diseases and indications resulting from the over-expression of matrix metalloendoproteinases such as found in certain metastatic tumour cell lines or other diseases mediated by the matrix metalloendoproteinases or increased TNF production, the compounds of formula (I) may be administered orally, topically, parenterally, by inhalation spray or rectally in dosage unit formulations containing non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats etc, the compounds of the invention are effective in the treatment of humans.

The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyeryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules where in the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occuring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation or an aqueous suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally- occuring gums, for example gum acacia or gum tragacanth, naturally-occuring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be in a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc containing the compounds of Formula (I) are employed. (For purposes of this application, topical application shall include mouth washes and gargles.)

Dosage levels of the order of from about 0.05 mg to about 140 mg per kilogram of body weight per day are useful in the treatment of the above- indicated conditions (about 2.5 mg to about 7 gms per patient per day). For example, inflammation may be effectively treated by the administration of from about 0.01 to 50 mg of the compound per kilogram of body weight per day (about 0.5 mg to about 3.5 gms per patient per day).

The amount of active ingredient that may be combined with the carrier materials to produce a single dosage form will vary depending upon the host treated and the particular mode of administration. For example, a formulation intended for the oral administration of humans may vary from about 5 to about 95 percent of the total composition. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. The following non-limiting Examples are intended to illustrate the preparation of compounds of Formula (I), and as such are not intended to limit the invention as set forth in the claims appended thereto.

In the Examples, the following abbreviations are used:
RT Room temperature
DCC Dicyclohexylcarbodiimide
EDC 1-(3-Dimethylaminopropyl)-3-ethylcarbodiimide hydrochloride
TNFα Tumour necrosis factor α
LPS Lipopolysaccharide
ELISA Enzyme linked immunosorbent assay
Intermediate 1 (R,S)-[2-(Acetylsulphanyl)-5-phthalimido] pentanoic acid
Intermediate 2 (S)-[2-(Acetylsulphanyl)-5phthalimido] pentanoic acid
Intermediate 3 (R)-[2-(Acetylsulphanyl)-5-phthalimido] pentanoic acid These three Intermediates were prepared according to the procedure described in WO-A-9611209.
Intermediate 4 (S)-[(1,1-Dimethylethoxy)carbonyl]-2-naphthylalanine This Intermediate was prepared by the procedure in WO-A-9611209 for (S)-[(1,1-dimethylethoxy)carbonyl]-4-thiazolyalanine. A general method is as follows:

Diethylacetamidomalonate was added to a stirred solution of sodium methoxide in methanol at room temperature. A yellow solution resulted, which was heated to 42° C. and treated in several portions with 2-bromomethyl naphthalene over the course of 2 h. The opaque solution gradually became translucent, and the internal temperature increased to 68° C. Water was then added and the resulting yellow solution allowed to cool overnight. The mixture was then re-heated to 65° C. and 46–48% sodium hydroxide solution was then added over a 2 h. The mixture was then allowed to cool overnight. The mixture was adjusted to pH 9 with 6M HCl and the solution stirred at 26° C. Following a dichloromethane work-up, the N-acetyl acid was subjected to biotransformation using amino acylase at pH 8, followed by Boc protection using Boc anhydride (1.1 equiv) in methanol at 0° C. The product was isolated as a white solid.

Intermediate 5 (S)-[(1,1-Dimethylethoxy)carbonyl]-2-naphthylalanine N-methylamide A solution of Intermediate 4 (12.06 g) in tetrahydrofuran (121 ml, 10 vols) at 0° C. under a nitrogen blanket was treated with DCC (1.1 equiv., 8.67 g) and N-hydroxysuccinimide (1.1 equiv., 4.84 g). A white precipitate formed. After 3 h stirring at 0° C. the precipitate was filtered and the residue washed with the minimum volume of tetrahydrofuran. The filtrate was then cooled to 0° C. and treated dropwise with aqueous methylamine (40% aqueous solution, 3.0 equiv., 9.61 ml). The precipitate was filtered and the residue washed with tetrahydrofuran. The filtrate was evaporated in vacuo to give the product as a white solid which was used directly in the next step. TLC $R_f$ 0.75 (EtOAc).

Intermediate 6 2-Naphthylalanine N-methylamide

A solution of Intermediate 5 (12.46 g) in dichloromethane (124 ml) at 0° C. was treated dropwise with neat trifluoroacetic acid (120 ml). The resulting pale yellow solution was allowed to reach room temperature over 48 h. The solvent was subsequently removed and the crude product dissolved in the minimum volume of 1N hydrochloric acid at 0° C. The aqueous phase was extracted with dichloromethane to remove any impurities. The aqueous phase was then taken to pH 8.5, initially using solid sodium bicarbonate and then a few drops of 3N sodium hydroxide. A white precipitate formed which was filtered, and the residue washed with water and dried in vacuo (7.2 g 83%). TLC $R_f$ 0.10 (EtOAc).

EXAMPLE 1

(S)-[2-(Acetylsulphanyl)-5-phthalimido]pentanoyl-(S)-2-naphthylalanine N-methylamide A solution of Intermediate 5 (0.29 g) in dichloromethane (5.8 ml) at 0° C. was treated with Intermediate 2 (0.41 g). EDC (0.267 g) and N-hydroxybenzatriazole (0.18 g) were then added and the resulting pale yellow solution was stirred under a nitrogen blanket overnight. 1N hydrochloric acid (2 mL) was added and the mixture shaken thoroughly; N-hydroxybenzatriazole precipitated from the acid phase and was removed by filtration. The organic phase was evaporated in vacuo to give the title compound as a white solid (75%). TLC $R_f$ 0.7 (EtOAc).

Similarly prepared were:

EXAMPLE 2

(R)-[2-(Acetylsulphanyl)-5-phthalimido]pentanoyl-(S)-2-naphthylalanine N-methylamide From Intermediate 3 and Intermediate 5, as a white solid (80%). TLC $R_f$ 0.72 (EtOAc).

EXAMPLE 3

(R, S)-[2-(Acetylsulphanyl)-5-phthalimido]pentanoyl-(S)-2-naphthylalanine N-methylamide From Intermediate 1 and Intermediate 5, as a white solid (77%). TLC $R_f$ 0.68 (EtOAc).

EXAMPLE 4

(R)-[2-(Sulphanyl)-5-phthalimido]pentanoyl-(S)-2-naphthylalanine N-methylamide

A solution of Example 3 (0.80 g) in methanol (16 ml) at 0° C. was treated with aqueous ammonia (3.2 ml) under a nitrogen blanket. The clear, colourless solution was stirred at 0° C. for 2 h. The solution was directly preadsorped onto silica and purified using flash column chromatography on a de-gassed column, eluting with 3% methanol in dichloromethane to liberate the title compound as a white solid (0.3 g, 41%) TLC $R_f$ 0.4 (EtOAc)

Similarly prepared were:

EXAMPLE 5

(S)-[2-(Sulphanyl)-5-phthalimido]pentanoyl-(S)-2-naphthylalanine N-methylamide

From Example 1, as a white solid (52%). TLC $R_f$ 0.38 (EtOAc)

EXAMPLE 6

(R,S)-[2-(Sulphanyl)-5phthalimido]pentanoyl-(S)-2-naphthylalanine N-methylamide

From Example 3, as a white solid (48%). TLC $R_f$ 0.42 (EtOAc)

Example A

Collagenase Inhibition Activity

The potency of compounds of general formula (I) to act as inhibitors of collagenase was determined by the procedure of Cawston and Barrett, (Anal. Biochem., 99:340–345, 1979) whereby a 1 mM solution of the inhibitor being tested or dilutions thereof was incubated at 37° C. for 16 hours with collagen and collagenase (buffered with 50 mM Tris, pH 7.6 containing 5 mM $CaCl_2$, 0.05% Brij 35, 60 mM NaCl and 0.02% $NaN_3$). The collagen was acetylated $^3H$ or $^{14}C$-collagen prepared by the method of Cawston and Murphy (Methods in Enzymolgy, 80:711, 1981). The choice of radiolabel did not alter the ability of collagenase to degrade the collagen substrate. The samples were centrifuged to sediment undigested collagen and an aliquot of the radioactive supernatant removed for assay on a scintillation counter as a measure of hydrolysis. The collagenase activity in the presence of 1 mM inhibitor, or a dilution thereof, was compared to activity in a control devoid of inhibitor and the results reported as that inhibitor concentration effecting 50% inhibition of the collagenase ($IC_{50}$).

Example B

Stromelysin Inhibition Activity

The potency of compounds of general formula (I) to act as inhibitors of stromelysin was determined using the procedure of Nagase et al (Methods in Enzymology Vol 254, 1994), whereby a 0.1 mM solution of the inhibitor being tested or dilutions thereof was incubated at 37° C. for 16 hours with stromelysin and $^3H$ transferrin (buffered with 50 mM Tris, pH 7.6 containing 10 mM $CaCl_2$, 150M NaCl, 0.05% Brij, 35, and 0.02% $NaN_3$). The transferrin was carboxymethylated with $^3H$ iodoacetic acid. The stromelysin activity in the presence of 1 mM, or a dilution thereof, was compared to activity in a control devoid of inhibitor and the results reported as that inhibitor concentration effecting 50% inhibition of the stromelysin ($IC_{50}$)

Example C

Gelatinase Inhibition Activity

The potency of the compounds of general formula (I) to act as inhibitors of gelatinase was determined using the procedure of Harris & Krane (Biochem Biophys. Acta, 258:566–576, 1972), whereby a 1 mM solution of the inhibitor being tested or dilutions thereof was incubated at 37° C. for 16 hours with gelatinase and heat denatured $^3H$ or $^{14}C$-acetylated collagen (buffered with 50 mM Tris, pH 7.6 containing 5 mM $CaCl_2$, 0.05% Brij 35 and 0.02% $NaN_3$). The $^3H$ or $^{14}C$ gelatin was prepared by denaturing $^3H$ or $^{14}C$-collagen produced according to the method of Cawston and Murphy (Methods in Enzymology, 80:711, 198 1) by incubation at 60° C. for 30 minutes. Undigested gelatin was precipitated by addition of trichloroacetic acid and centrifugation. The gelatinase activity in the presence of 1 mM, or dilution thereof, was compared to the activity in a control devoid of inhibitor and results reported as that inhibitor concentration effecting 50% inhibition of the gelatinase ($IC_{50}$).

Example D
MMP Inhibition Activity-Fluorimetric Assay

The potency of compounds of general formula (I) to act as inhibitors of collagenase-1(MMP-1), collagenase-2 (MMP-8), collagenase-3 (MMP-13), gelatinase-A (MMP-2), gelatinase-B (MMP-9) and stromelysin-1 (MMP-3) was determined using the following procedure:

Inhibitors are dissolved in dimethylsulphoxide containing 0.02% β-mercaptoethanol and serial dilutions are prepared. Activated enzyme is incubated in assay buffer containing 50 mM Tris, pH 7.4, 5 mM $CaCl_2$, 0.002% $NaN_3$ and Brij 35 in the presence and absence of inhibitor. Samples are pre-incubated at 37° C. for 15 minutes before the addition of the fluorimetric substrate (Mca-Pro-Leu-Gly-Leu-Dpa-Ala-Arg-$NH_2$) to a final concentration of 10 μM. The assay is incubated for 20–30 min at 37° C. and then read in a Fluoroscan II at $\lambda_{ex}$ (340 nm) and $\lambda_{em}$ (405 nm).

The enzyme activity was compared to activity in a control devoid of inhibitor and the results reported as that inhibitor concentration effecting 50% inhibition of the stromelysin ($IC_{50}$).

Example E
Inhibition of TNF α Production

The potency of the compounds of general formula (I) to act as inhibitors of the production of TNFα is determined using the following procedure. A 100 μM solution of the inhibitor being tested or dilutions thereof is incubated at 37° C. in an atmosphere of 5% $CO_2$ with THP-1 cells (human monocytes) suspended in RPM1 1640 medium and 20 μM β-mercaptoethanol at a cell density of $1\times10^6$/ml and stimulated with LPS. After 18 hours the supernatant is assayed for the levels of TNF α using a commercially available ELISA kit (R & D Systems).

The activity in the presence of 0.1 mM inhibitor or dilutions thereof is compared to activity in a control devoid of inhibitor and results reported as that inhibitor concentration effecting 50% inhibition of the production of TNFα.

Example F
Inhibition of L-Selectin Shedding

Compounds of general formula (I) are evaluated in an assay of L-selectin shedding by peripheral blood mononuclear cells (PBMC). PBMC are isolated from buffy coats by standard procedures using Ficoll. A 100 μM solution of the inhibitor being tested or dilutions thereof is incubated for 20 min at 37° C. in an atmosphere of 5% $CO_2$ with $4\times10^6$/ml PBMC stimulated with PMA. The cells are centrifuged down and the supernatants tested for sL-selectin using a commercially available ELISA kit (R & D Systems).

The activity in the presence of 100 μM inhibitor or dilutions thereof was compared to activity in a control devoid of inhibitor and results reported as that inhibitor concentration effecting 50% inhibition of the shedding of L-selectin.

Example G
Inhibition of SIl-1RII Shedding

Compounds of general formula (I) are evaluated in an assay of sIl-1RII shedding by peripheral blood mononuclear cells (PBMC). PBMC are isolated from buffy coats by standard procedures using Ficoll. A 100 μM solution of the inhibitor being tested or dilutions thereof are incubated for 18 h at 37° C. in an atmosphere of 5% $CO_2$ with $2\times10^6$/ml PBMC stimulated with Il-13. The cells are centrifuged down and the supernatants tested for SIl-1RII using a commercially available ELISA kit (R & D Systems).

The activity in the presence of 100 μM inhibitor or dilutions thereof is compared to activity in a control devoid of inhibitor and results reported as that inhibitor concentration effecting 50% inhibition of the shedding of sIl-1RII.

Example H
Inhibition of Il-6R Shedding

Compounds of general formula (I) are evaluated in an assay of sIl-6R shedding by HL-60 cells. PBMC are isolated from buffy coats by standard procedures using Ficoll. A 100 μM solution of the inhibitor being tested or dilutions thereof is incubated for 24 h at 37° C. in an atmosphere of 5% $CO_2$ with $2\times10^6$/ml HL-60 cells stimulated with PMA The cells are centrifuged down and the supernatants tested for sIl-6R using a commercially available ELISA kit (R & D Systems).

The activity in the presence of 100 μM inhibitor or dilutions thereof is compared to activity in a control devoid of inhibitor and results reported as that inhibitor concentration effecting 50% inhibition of the shedding of Il-6R.

Example I
Inhibition of TNF RII Shedding

The potency of the compounds of general formula (I) to act as inhibitors of the shedding of TNF RII is determined using the following procedure. A 100 μM solution of the inhibitor being tested or dilutions thereof are incubated at 37° C. in an atmosphere of 5% $CO_2$ with THP-1 cells (human monocytes) suspended in RPM1 1640 medium and 20 μM β-mercaptoethanol at a cell density of $1\times10^6$/ml and stimulated with LPS. After 18 hours the supernatant is assayed for the levels of sTNF RII using a commercially available ELISA kit (R & D Systems).

The activity in the presence of 0.1 mM inhibitor or dilutions thereof is compared to activity in a control devoid of inhibitor and results reported as that inhibitor concentration effecting 50% inhibition of the shedding of TNF RII.

Example J
Adjuvant Arthritic Rat Model

Compounds of general formula (I) were evaluated in an adjuvant arthritis model in the rat based on the methods employed by B. B. Newbould (1963), Br.J.Pharmacol, 21, 127–136 and C. M. Pearson and F. D. Wood (1959), Arthritis Rheum, 2, 440–459. Briefly male Wistar rats (180–200 g) were injected at the base of the tail with Freund's adjuvant. Twelve days later the responding animals were randomised into experimental groups. Compounds of general formula (I) were dosed either orally as a suspension in 1% methyl cellulose or intraperitoneally in 0.2% carboxymethylcellulose from day 12 to the end of the experiment on day 22. Hind paw volumes were measured every two days from day 12 onwards and X-rays were taken of the hind feet on completion of the experiment. Results were expressed as the percent increase of foot volume over day 12 values.

Example K
Mouse Ovarian Carcinoma Xenograft Model

Compounds of general formula (I) were evaluated in an ovarian carcinoma xenograft model of cancer, based on that described by B. Davies et al (1993), Cancer Research, 53, 2087–2091 This model, in brief, consists of inoculating female nu/nu mice with 1×10⁹ OVCAR3-icr cells into the peritoneal cavity. Compounds of general formula (I) are administered by the oral route as a suspension in 1% methyl cellulose or intraperitoneally as a suspension in phosphate buffered saline in 0.01% Tween-20. At the conclusion of the experiment (4–5 weeks) the number of peritoneal cells are counted and any solid tumour deposits weighed. In some experiments tumour development is monitored by measurement of tumour specific antigens.

Example L
Rat Mammary Carcinoma Model

Compounds of general formula (I) were evaluated in a HOSP.1 rat mammary carcinoma model of cancer (S.Eccles et al (1995), Cancer Research, in press). This model consists of the intravenous inoculation of female CBH/cbi rats with 2×10⁴ tumour cells into the jugular vein. Compounds of general formula (I) are administered by the oral route as a suspension in 1% methyl cellulose or intraperitoneally as a suspension in phosphate buffered saline+0.01% Tween-20. At the conclusion of the experiment (4–5 weeks) the animals are killed, the lungs are removed and individual tumours counted after 20 hours fixation in Methacarn.

Example M
Mouse B16 Melanoma Model

The anti-metastatic potential of compounds of general formula (I) is evaluated in a B16 melanoma model in C57BL/6. Mice are injected intravenously with 2×10⁵ B16/F10 murine tumour cells harvested from in vitro cultures. Inhibitors are administered by the oral route as a suspension in 1% methyl cellulose or intraperitoneally as a suspension in phosphate buffered saline pH7.2+0.01% Tween-20. Mice are killed 14 days after cell inoculation and the lungs removed and weighed prior to fixing in Bouin's solution. The number of colonies present on the surface of each set of lungs is then counted by eye.

These assay procedures may also be found in the copending Application claiming priority from British Patent Applications Nos. 9616599.8, filed 7th Aug. 1996, and 9707427.2.

We claim:

1. A compound of general formula (I):

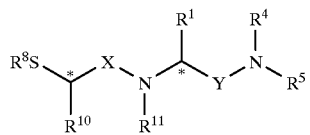

wherein X is selected from the group consisting of C=O and C=S;
Y is selected from the group consisting of C=O, C=S and S(O)$_m$ where m=1–2;
R$^1$ is C$_{0-4}$-alkyl-R$^2$;
R$^2$ is naphthyl or quinolinyl optionally substituted with R$^3$;
R$^3$ is selected from the group consisting of R$^{20}$, C$_{1-4}$-alkyl, and C$_{1-4}$-alkyl substituted with R$^{20}$; with the provisos that:
  (a) when R$^2$ is a napthyl group substituted with R$^3$, then R$^3$ is not OR$^6$; and
  (b) when R$^3$ is NR$^6$ CO$_2$R$^7$, then R$^7$ is not hydrogen;
R$^4$ and R$^5$ are the same or different and are each selected from the group consisting of H and C$_{1-4}$-alkyl;
R$^6$ is selected from the group consisting of H, C$_{1-4}$-alkyl, aryl, C$_{1-4}$-alkyl-aryl, heteroaryl, and C$_{1-4}$-alkyl-heteroaryl, and each R$^6$ in N(R$^6$)$_2$ may be the same or different;
R$^7$ is selected from the group consisting of H, C$_{1-4}$-alkyl, C$_{1-4}$-alkyl-aryl and C$_{1-4}$-alkyl-heteroaryl;
R$^8$ is selected from the group consisting of H and COR$^9$;
R$^9$ is selected from the group consisting of C$_{1-4}$ alkyl, aryl, heteroaryl, C$_{1-4}$ alkyl-aryl and C$_{1-4}$ alkyl-heteroaryl;
R$^{10}$ and R$^{11}$ are the same or different and are selected from the group consisting of hydrogen, R$^{21}$, and R$^{21}$ substituted with R$^{12}$;
R$^{12}$ is selected from the group consisting of COR$^{13}$, NR$^6$R$^{14}$, phthalimido, any of the groups:

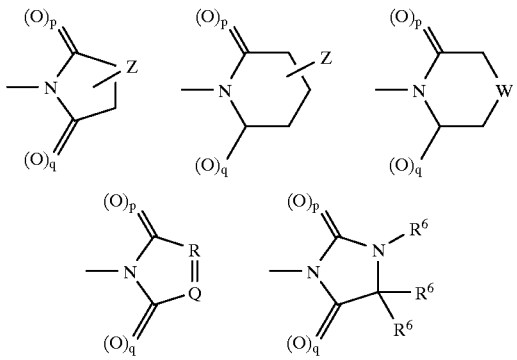

where p and q are 0 or 1 and are the same or different, and AR$^9$ wherein A is O, NR$^9$ or S(O)$_n$ where n=0–2 and, if A=NR$^9$ the groups R$^9$ may be the same or different;
R and Q are selected from the group consisting of CH and N and are the same or different;
W is selected from the group consisting of O, S(O)$_n$ and NR$^{15}$, wherein n=0–2;
Z is selected from the group consisting of H and C$_{0-4}$ alkyl-R$^{18}$ and may be attached to any available position on the ring;
R$^{13}$ is selected from the group consisting of OR$^7$, N(R$^6$)$_2$, C$_{1-4}$ alkyl, aryl, C$_{1-4}$ alkyl-aryl, heteroaryl, and C$_{1-4}$ alkyl-heteroaryl;
R$^{14}$ is selected from the group consisting of COR$^6$, CO$_2$R$^7$, CON(R$^6$)$_2$, SO$_2$R$^{16}$ and COR$^{16}$, with the proviso that when R$^{14}$ is CO$_2$R$^7$, then R$^7$ is not H;
R$^{15}$ is selected from the group consisting of H, C$_{1-4}$ alkyl, COR$^9$, CO$_2$R$^{19}$, CON(R$^6$)$_2$, and SO$_2$R$^9$;
R$^{16}$ is C$_{1-4}$ alkyl optionally substituted with R$^{17}$;
R$^{17}$ is selected from the group consisting of CO$_2$R$^6$, CON(R$^6$)$_2$, N(R$^6$)$_2$, SO$_2$R$^9$, and any of the groups:

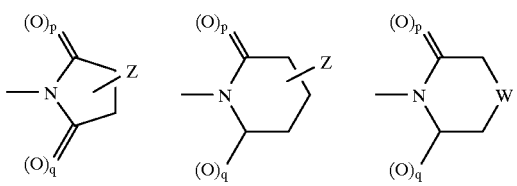

-continued

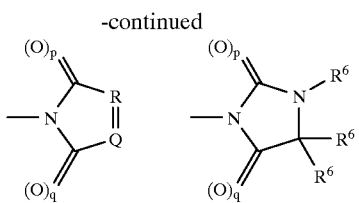

$R^{18}$ is selected from the group consisting of $CO_2R^6$, $CON(R^6)_2$, $N(R^6)_2$, and $NHCO_2R^{19}$; and $R^{19}$ is selected from the group consisting of $C_{1-4}$ alkyl, $C_{1-4}$ alkyl-aryl, and $C_{1-4}$ alkyl-heteroaryl;

$R^{20}$ is selected from the group consisting of aryl, heteroaryl, halogen, $OR^6$, $N(R^6)_2$, $CO_2R^7$, $COR^6$, $CON(R^6)_2$, $SO_nR^6$ wherein n=0–2, $SO_2N(R^6)_2$, $NR^6COR^6$, $NR^6CO_2R^7$, $NR^6CON(R^6)_2$, and $NR^6SO_2R^6$;

$R^{21}$ selected from the group consisting of $C_{1-6}$ alkyl, aryl, $C_{1-6}$ alkyl-aryl, heteroaryl, $C_{1-6}$ alkyl-heteroaryl, cyclo$(C_{3-6})$alkyl, $C_{1-6}$ alkyl-cyclo$(C_{3-6})$alkyl, heterocyclo$(C_{4-6})$alkyl and $C_{1-4}$ alkyl-heterocyclo$(C_{4-6})$alkyl;

or a salt, solvate, hydrate or protected amino or protected carboxy derivative thereof.

2. The compound, according to claim 1, wherein X is C=O.

3. The compound, according to claim 1, wherein Y is selected from the group consisting of C=O and $SO_2$.

4. The compound, according to claim 1, wherein $R^{10}$ and $R^{11}$ are the same or different and are selected from the group consisting of H and optionally-substituted alkyl, alkyl-aryl, alkyl-heteroaryl, alkyl-cycloalkyl, and alkyl-heterocycloalkyl.

5. The compound, according to claim 1 wherein $R^{12}$ is selected from the group consisting of $NR^6R^{14}$ and phthalimido.

6. The compound, according to claim 1, which is selected from the group consisting of (S)-[2-(Acetylsulphanyl)-5-phthalimido]pentanoyl-(S)-2-naphthylalanine N-methylamide;

(R)-[2-(Acetylsulphanyl)-5-phthalimido]pentanoyl-(S)-2-naphthylalanine N-methylamide;

(R,S)-[2-(Acetylsulphanyl)-5-phthalimido]pentanoyl-(S)-2-naphthylalanine N-methylamide;

(R)-[2-(Sulphanyl)-5-phthalimido]pentanoyl-(S)-2-naphthylalanine N-methylamide;

(S)-[2-(Sulphanyl)-5-phthalimido]pentanoyl-(S)-2-naphthylalanine N-methylamide; and (R,S)-[2-(Sulphanyl)-5-phthalimido]pentanoyl-(S)-2-naphthylalanine N-methylamide.

7. The compound, according to claim 1, which is a single enantiomer.

8. A pharmaceutical composition, comprising a compound of claim 1, and a pharmaceutically-acceptable diluent or carrier.

9. A method for the treatment or prevention of a condition associated with matrix metalloproteinasees or that is mediated by TNF α or enzymes involved in the shedding of L-selectin, the TNF receptors, or IL-6 receptors, wherein said method comprises the administration of an effective amount of a compound of claim 1.

10. The method, according to claim 9, where in said condition is selected from cancer, inflammation and inflammatory diseases, tissue degeneration, periodontal disease, ophthalmological disease, dermatological disorders, fever, cardiovascular effects, haemorrahage, coagulation and acute phase response, cachexia, anorexia, acute infection, HIV infection, shock states, graft versus host reactions, autoimmune disease, reperfusion injury, meningitis, and migraine.

11. The method, according to claim 9, wherein said condition is selected from tumor growth, angiogenesis, tumor invasion and spread, metastases, malignant ascites, and malignant pleural effusion.

12. The method, according to claim 9, wherein said condition is selected from cerebral ischaemia, ischaemic heart disease, rheumatoid arthritis, osteoarthritis, osteoporosis, asthma, multiple sclerosis, neurodegeneration, Alzheimer's, atherosclerosis, stroke, vasculitis, Crohn's disease, and ulcerative colitis.

13. The method, according to claim 9, wherein said condition is selected from corneal ulceration, retinopathy and surgical wound healing.

14. The method, according to claim 9, wherein said condition is selected from psoriasis, atopic dermatitis, chronic ulcers, and epidermolysis bullosa.

15. The method, according to claim 9, wherein said condition is selected from periodontitis and gingivitis.

16. The method, according to claim 9, wherein said condition is selected from rhinitis, allergic conjunctivitis, eczema, and anaphylaxis.

17. The method, according to claim 9, wherein said condition is selected from restenosis, congestive heart failure, endometriosis, athersclerosis, and endosclerosis.

* * * * *

UNITED STATES PATENT AND TRADEMARK OFFICE
CERTIFICATE OF CORRECTION

PATENT NO. : 5,955,435
DATED : September 21, 1999
INVENTOR(S) : Andrew Douglas Baxter, John Gary Montana It is certified that error appears in the above-identified patent and that said Letters Patent is hereby corrected as shown below:

Column 20, line 14: "where in" should read --wherein--.

Signed and Sealed this

Twenty-fifth Day of April, 2000

Attest:

Q. TODD DICKINSON

*Attesting Officer*  *Director of Patents and Trademarks*